United States Patent
Juergens

(10) Patent No.: US 11,439,466 B2
(45) Date of Patent: Sep. 13, 2022

(54) OPERATING METHOD FOR A MEDICAL SYSTEM, AND MEDICAL SYSTEM FOR PERFORMING A SURGICAL PROCEDURE

(71) Applicant: OLYMPUS Winter & Ibe GmbH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 191 days.

(21) Appl. No.: 16/406,696

(22) Filed: May 8, 2019

(65) Prior Publication Data
US 2019/0343588 A1 Nov. 14, 2019

(30) Foreign Application Priority Data
May 9, 2018 (DE) ..................... 10 2018 111 180.0

(51) Int. Cl.
*G16H 30/40* (2018.01)
*G16H 20/40* (2018.01)
(Continued)

(52) U.S. Cl.
CPC ............ *A61B 34/10* (2016.02); *A61B 5/7267* (2013.01); *G06T 7/0012* (2013.01); *G16H 20/40* (2018.01);
(Continued)

(58) Field of Classification Search
CPC ... A61B 34/10; A61B 34/20; A61B 2090/365; G16H 30/40; G16H 20/40; G16H 50/70; G16H 40/40; G16H 70/60
See application file for complete search history.

(56) References Cited

U.S. PATENT DOCUMENTS 9,836,654 B1 * 12/2017 Alvi ..................... A61B 34/25
2013/0211232 A1    8/2013 Murphy et al.
(Continued)

FOREIGN PATENT DOCUMENTS

JP        2007/136160 A      6/2007
WO       2017/058710 A1      4/2017
WO    WO-2018060304 A1 *    4/2018 ............ A61B 34/10

OTHER PUBLICATIONS

Andersen, Daniel, et al. "Medical telementoring using an augmented reality transparent display." Surgery 159.6 (2016): 1646-1653. (Year: 2016).*
(Continued)

*Primary Examiner* — Linh Giang Le
*Assistant Examiner* — Constantine Siozopoulos
(74) *Attorney, Agent, or Firm* — Scully, Scott, Murphy & Presser, P.C.

(57) ABSTRACT

An operating method for a medical system for performing a surgical procedure, where the medical system includes at least one artificial intelligence, an intraoperative artificial intelligence and an output unit. The operating method including: supplying the intraoperative artificial intelligence with preoperative output data and intraoperative data; processing the preoperative output data and the intraoperative data by the intraoperative artificial intelligence; and outputting output data from the intraoperative artificial intelligence to the output unit that provides a user output based on the output data from the intraoperative artificial intelligence.

9 Claims, 2 Drawing Sheets

(51) Int. Cl.
  *A61B 34/10*    (2016.01)
  *G06T 7/00*    (2017.01)
  *A61B 5/00*    (2006.01)

(52) U.S. Cl.
  CPC ... *G16H 30/40* (2018.01); *G06T 2207/20084* (2013.01)

(56) References Cited

U.S. PATENT DOCUMENTS

| | | |
|---|---|---|
| 2013/0293578 A1 | 11/2013 | Leung |
| 2014/0081659 A1* | 3/2014 | Nawana ............... G16H 50/50 705/3 |
| 2016/0035093 A1 | 2/2016 | Kateb et al. |
| 2017/0083666 A1 | 3/2017 | Biancalana et al. |
| 2018/0168741 A1* | 6/2018 | Swayze ............... A61B 34/25 |

OTHER PUBLICATIONS

J. Zhang, et al., "Rapid surface registration of 3D volumes using a neural network approach", Image and Vision Computing, 2008, pp. 201-210. vol. 26, No. 2.

Japanese Office Action dated Jan. 5, 2021.

\* cited by examiner

OPERATING METHOD FOR A MEDICAL SYSTEM, AND MEDICAL SYSTEM FOR PERFORMING A SURGICAL PROCEDURE

CROSS-REFERENCE TO RELATED APPLICATION

The present application claims the benefit to DE 10 2018 111 180.0 filed on May 9, 2018, the entire contents of which is incorporated herein by reference.

BACKGROUND

Field

The present application relates to an operating method for a medical system for performing a surgical procedure comprising at least one artificial intelligence. Furthermore, the present application relates to a medical system for performing a surgical procedure.

Prior Art

Medical systems are generally known in various designs. The technical medical equipment of an operating room is for example to be considered a medical system. In a modern operating room, there are cameras for recording the performance of the operation, various surgical instruments, such as endoscopes, as well as imaging medical equipment like an X-ray machine. Playback units are also frequently known with which for example examination results recorded before surgery, such as MRT or CT images, can be displayed.

Artificial intelligence is increasingly being used in individual medical devices. Artificial intelligence is to be understood as a unit implemented in a computing device whose behavior or reaction to certain inputs from outsiders functions similarly to human intelligence. In this context, the term "artificial intelligence" comprises for example machine learning, mechanical vision and recognition of objects, voice recognition and voice processing, and robotics as well.

Machine learning is an artificial intelligence that can independently learn how to behave to achieve the highest possible assessment using a number of situations or processes in addition to the associated assessment. The assessment can either be dictated to the artificial intelligence or dictated by the artificial intelligence using a known assessment criterion, or be ascertained by the artificial intelligence itself. The artificial intelligence thus accumulates and contains the knowledge of optimum system operation adapted to the respective situation.

Mechanical vision and recognition of objects is for example the extraction of objects from images and/or the assignment of (extracted) objects to specific categories. Voice processing comprises for example the independent recognition of words and/or the recognition of commands and operating instructions from a freely spoken text.

It is common to train artificial intelligence before its use. It is even frequently provided to train the artificial intelligence exclusively beforehand and leave it unchanged for the duration of use. It is however also common for the artificial intelligence to perform an assessment of the evaluation results at the same time as ascertaining the evaluation results, and to retrain itself using the assessment.

SUMMARY

It is an object to provide an operating method for a medical system in which the use of artificial intelligence is to be improved.

Such object can be solved by an operating method for a medical system for performing a surgical procedure comprising at least one artificial intelligence, wherein the operating method is developed in that the system comprises an intraoperative artificial intelligence and an output unit, wherein the intraoperative artificial intelligence is supplied with preoperative output data and intraoperative data, and the preoperative output data and the intraoperative data are processed by the intraoperative artificial intelligence, wherein output data from the intraoperative artificial intelligence are output to the output unit that provides the user output based on the output data from the intraoperative artificial intelligence.

The preoperative output data can be results of mechanical preprocessing as well as the results of preprocessing done manually.

According to an embodiment, the system can comprise a preoperative artificial intelligence, wherein preoperative data are supplied to the preoperative artificial intelligence and processed by the preoperative artificial intelligence and output as the preoperative output data, wherein the preoperative output data are supplied to the intraoperative artificial intelligence.

Various artificial intelligences can be combined with each other in order to thus achieve optimum support of the medical personnel. The medical system delivers user output in which preoperative and intraoperative data are combined optimally with each other by means of artificial intelligence.

The artificial intelligence that is used can be selected and specified as needed and depending on the application. The type of the first artificial intelligence and the second artificial intelligence can be of the same type or also differ from each other. For example, the artificial intelligence can be configured as a computer, one or more processors and/or circuits, or any other artificial intelligence known in the art, such as an artificial neural net or network (artificial neural network) as a support vector machine, as a decision tree, as a Bayesian belief network, as so-called k-nearest neighbors, as a self-organizing map, as case-based reasoning, as instance-based learning, or also as a so-called hidden Markov model. Of course, combinations of these designs are also possible.

According to one embodiment, the artificial intelligence, and this relates to both preoperative as well as intraoperative artificial intelligence, can be configured as an artificial neural network, such as, a deep neural network (DNN). Image data or acoustic data as well can be effectively processed with such an artificial intelligence. It is likewise provided to equip a single artificial intelligence with a plurality of neural networks, wherein different network types can be used and can be combined with each other.

According to an embodiment, the preoperative data can comprise first image data of at least one imaging medical device, and the preoperative artificial intelligence processes the first image data with respect to an anatomy and/or pathology present in the first image data, and outputs the anatomical data characterizing the anatomy and/or the pathology data characterizing the pathology as preoperative output data.

The preoperative artificial intelligence can extract information from the preoperative first image data that for example are CT or MRT image data. Physiological or pathological structures can be identified directly in the image data in order to optimally support the medical personnel during the surgical procedure. According to another embodiment, the preoperative artificial intelligence can analyze data of a physician's letter or a finding as preoperative data. The corresponding analysis can be combined with the analysis of the image data; for example, the pathological structures mentioned in the finding or the physician's letter can be identified in the image data.

According to another embodiment, the intraoperative data can comprise second image data, and the intraoperative artificial intelligence can process the second image data in that notes are added to the second image data, and the second image data are processed into image data with augmented reality and are provided as user output.

The intraoperative artificial intelligence can extract information from real-time images that are recorded by one or more cameras which are installed in an operation room. Processing these images as images with augmented reality makes it easier for the medical personnel to be oriented in the surgical field. In addition, help can be offered individually and situationally in that corresponding objects or regions of the recorded images are marked in color or are provided with comments.

According to another embodiment, the intraoperative artificial intelligence can add additional information relating to the anatomy data and/or the pathology data to the notes. It is therefore possible to provide to the user the anatomy data and/or pathology data output by the preoperative artificial intelligence as comments in an image data output with augmented reality. Anatomical or pathological structures can for example be marked in real-time images or provided with instructions.

The intraoperative artificial intelligence can process the second image data in that indicator recognition and/or object recognition is performed in the second image data, and the intraoperative artificial intelligence can add additional information to the notes based on the anatomy data and/or pathology data, additionally taking into account the results of the indicator recognition.

Since the intraoperative artificial intelligence considers additional results of an indicator recognition, the information provided in the notes can be further improved or expanded. "Indicator recognition" in this context is to be understood both as object recognition as well as so-called "landmark recognition", i.e., a recognition of certain indicators in the image data.

According to another embodiment, the intraoperative data can comprise parameters and/or operating data of at least one intraoperatively operated medical device, and the intraoperative artificial intelligence can add to the notes additional information on the parameters and/or operating data of the at least one intraoperatively operated medical device.

For example, selected handling effects, temperatures of the surgical instruments used, working voltages, current strengths, and the like can be understood as parameters and operating data. These parameters and/or operating data of the medical device can be added as notes to the image data with augmented reality. It is however also provided to process the corresponding operating data or parameters by means of intraoperative artificial intelligence, and for example issue a warning when significant deviations are determined in certain situations. The output of such a warning message can be done acoustically or visually via any desired user interface or any desired user output unit.

According to another embodiment, the intraoperative artificial intelligence can process the second image data with respect to at least one surgical instrument visible in the second image data and used intraoperatively, and the surgical instrument generates characteristic instrument data and adds information to the notes relating to the surgical instrument used.

The recognition of the intraoperatively used surgical instrument makes it possible to offer various additional aids or assistance functions, for example to propose a change of an instrument, when it is recognized in the intraoperatively detected image data that the selected instrument may be unsuitable. In this context, the surgical instrument used can be recognized by evaluating the image data. If in other words at least part or a section of a medical or surgical instrument is imaged in the image data, the instrument can therefore be recognized.

According to another embodiment, the intraoperative artificial intelligence can process the second image data in that a method status of a surgical procedure is recognized, wherein additional information regarding the method status of the surgical procedure can be added to the notes.

Safety and quality control can be realized from recognizing and analyzing the method status, i.e., the current phase of the surgical procedure. For example, a warning message can be output when a significant deviation from a typical progression of a specific surgical procedure is determined.

According to another embodiment, the intraoperative data can comprise parameters and/or operating data of at least one intraoperatively operated medical device, and the intraoperative artificial intelligence can process the parameters and/or operating data, and provide device information that characterizes an operating state and/or configuration of the at least one medical device as user output.

The device information can be output as comments in the image data with augmented reality, or output on any desired other output unit.

In this context, according to another embodiment, the intraoperative artificial intelligence can generate the device information additionally taking into account the anatomy data and/or the pathology data.

According to another embodiment, the intraoperative artificial intelligence can process the second image data in that a method status of the surgical procedure is recognized, wherein the device information is generated additionally taking into account the method status of the surgical procedure.

By processing the method status of the surgical procedure in combination with the device information, the surgical procedure can be logged which allows simplified quality control.

The individual processing steps can be performed in individual AI modules.

Processing steps that are performed in individual AI modules of the intraoperative artificial intelligence can be, for example: The recognition of a phase or state of the performed surgical procedure, providing image data with notes, providing user support, recognition of specific identifiers, performing object recognition, performing intraoperative anatomy and pathology recognition, performing instrument recognition, processing device data, performing depth calculation.

Processing steps that are performed in individual AI modules of the preoperative artificial intelligence can be, for example: Performing anatomy recognition and performing preoperative pathology recognition.

The intraoperative artificial intelligence and the preoperative artificial intelligence can be considered as AI modules.

According to another embodiment, a plurality of individual AI modules can be combined into one module group, wherein the AI modules can be linked together such that output data of a first AI module is supplied as input data to a second AI module.

The use of the artificial intelligence can be extremely flexible since the individual modules can be combined with each other as desired.

Such object can also solved by a medical system for performing a surgical procedure, said system comprising a plurality of AI modules that are configured to process intraoperative data in individual processing steps, wherein the AI modules are linked together such that output data of a first AI module are supplied as input data to a second AI module.

The same or similar advantages as already mentioned beforehand with respect to the operating method also apply to the medical system; repetitions will therefore be omitted.

BRIEF DESCRIPTION OF THE DRAWINGS

Further features will become apparent from the description of the embodiments together with the claims and the attached drawings. Embodiments can fulfill individual features or a combination of several features.

The embodiments are described below, without restricting the general idea of the invention, based on the exemplary embodiments in reference to the drawings, whereby we expressly refer to the drawings with regard to the disclosure of all details that are not explained in greater detail in the text. In the following.

DETAILED DESCRIPTION

Figure 1:
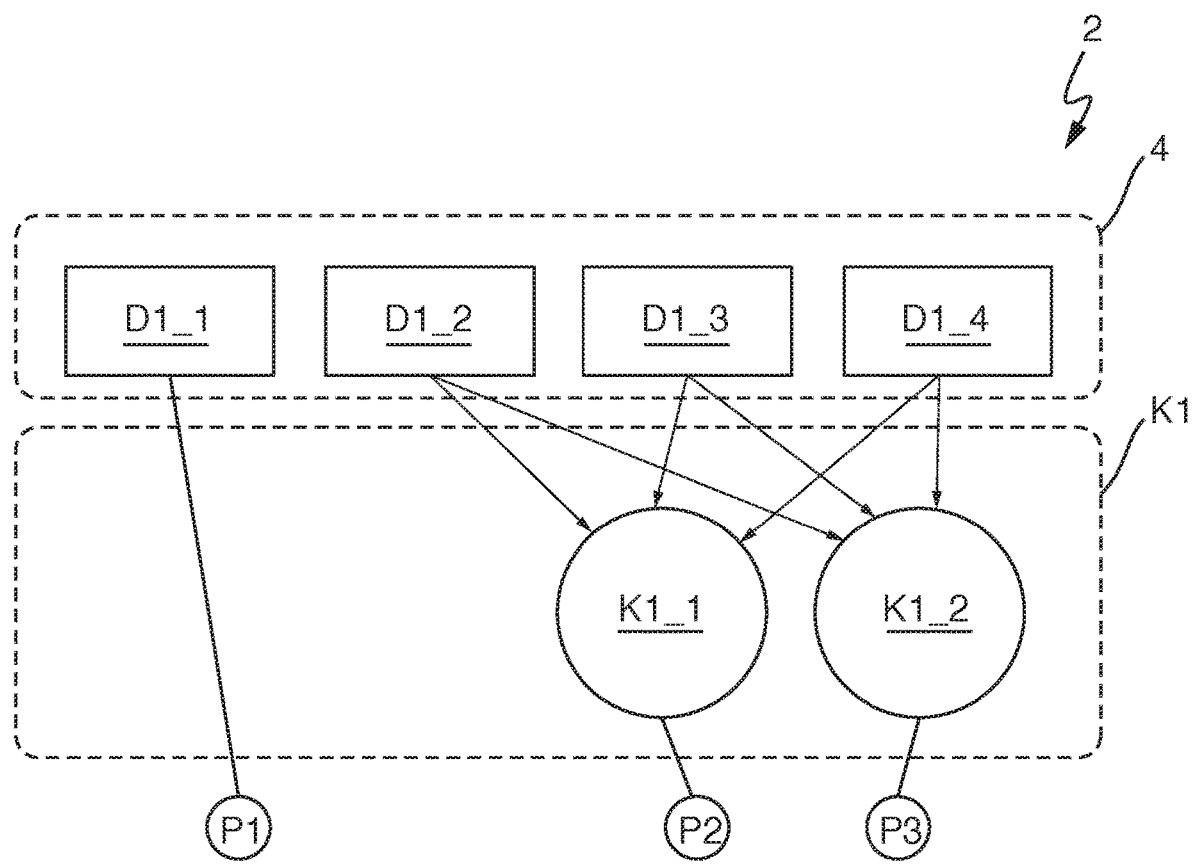
FIG. 1 illustrates a first part of a schematically simplified block diagram of a medical system for performing a surgical procedure.

In the drawings, the same or similar elements and/or parts are always provided with the same reference numbers; a reintroduction will therefore always be omitted.

FIG. 1 shows a schematic and simplified block diagram of a medical system 2, wherein only a section of the system 2 is portrayed in FIG. 1. The portrayed section of the medical system 2 comprises a preoperative data source 4 in which the preoperative data $D1\_1$ to $D1\_4$ are present that are generally also to be provided with reference sign D1. A preoperative artificial intelligence K1 is also present. The preoperative artificial intelligence K1 comprises a first AI module $K1\_1$ and a second AI module $K1\_2$.

Figure 2:
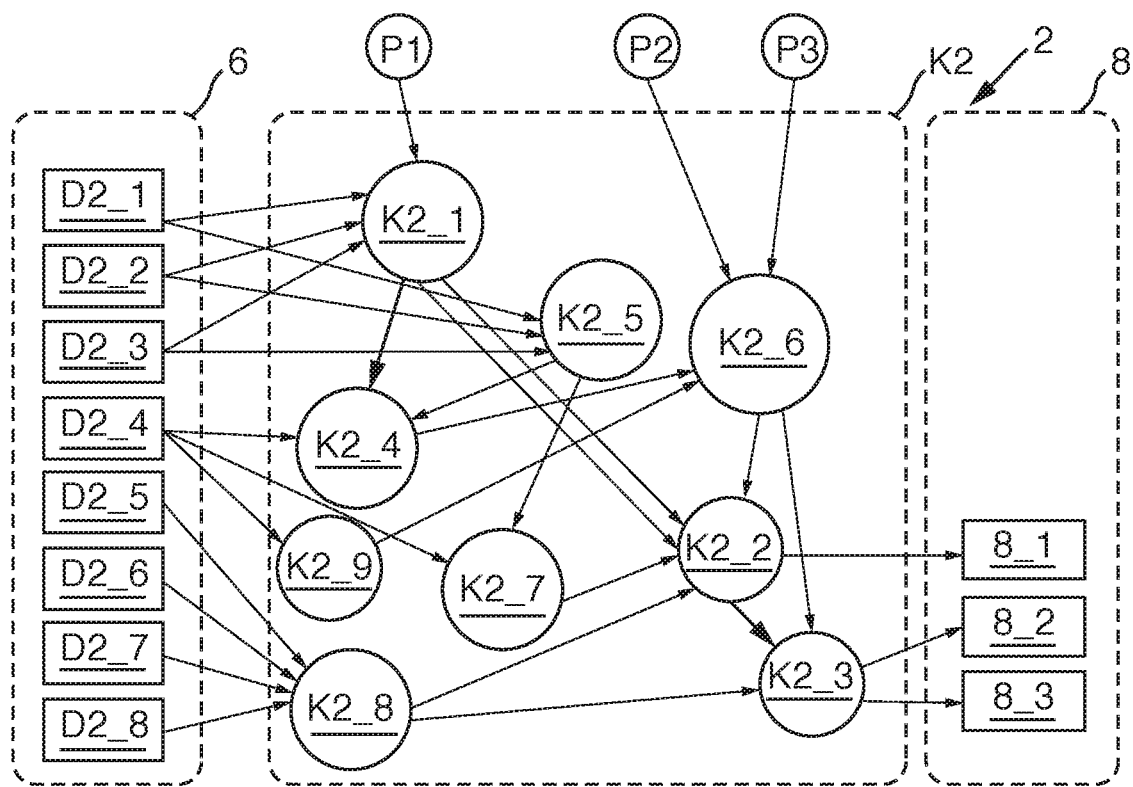
FIG. 2 illustrates a second part of a schematically simplified block diagram of a medical system for performing a surgical procedure.

The preoperative artificial intelligence K1 is connected to the parts or blocks of the medical system 2 shown in FIG. 2. FIG. 2 shows a schematically simplified block diagram of an intraoperative artificial intelligence K2, an intraoperative data source 6 and an output unit 8. The intraoperative data source 6 comprises different intraoperative data $D2\_1$ to $D2\_8$. The intraoperative artificial intelligence K2 comprises AI modules $K2\_1$ to $K2\_9$. The output unit 8 comprises output modules $8\_1$ to $8\_3$.

A data transfer to points P1, P2 and P3 occurs from the part of the medical system 2 portrayed in FIG. 1 to the part of the medical system 2 portrayed in FIG. 2.

The preoperative artificial intelligence K1 (the same also holds true for the first AI module $K1\_1$ and the second AI module $K1\_2$) as well as the intraoperative artificial intelligence K2 (the same of course also holds true for the AI modules $K2\_1$ to $K2\_9$) are artificial intelligences that are selected and combined with each other depending on the need and application. For example, the artificial intelligence can be an artificial neural net or network, a support vector machine, a decision tree, a Bayesian belief network, a self-organizing map, a network for case-based reasoning or for instance-based learning, or an artificial intelligence that is designed as a so-called hidden Markov model.

The medical system 2 is configured to perform a surgical procedure. For this, the medical system comprises a surgical instrument, such as an endoscope.

Preoperative data D1 are supplied to the preoperative artificial intelligence K1. The preoperative data D1 are for example a surgery plan $D1\_1$. Furthermore, the preoperative data D1 can be results of imaging medical methods such as image data $D1\_2$ from a CT image, image data $D1\_3$ from an MRT image, or a transfer letter $D1\_4$ from a physician. The preoperative data $D1\_1$ to $D1\_4$ can also comprise patient data.

The surgery plan $D1\_1$ is transferred directly via the transfer point P1 to the intraoperative artificial intelligence K2. The normal preoperative data $D1\_2$ to $D2\_4$ are supplied to the AI modules $K1\_1$ and $K1\_2$ of the preoperative artificial intelligence K1.

The preoperative artificial intelligence K1 comprises for example an artificial intelligence for anatomy recognition as a first AI module $K1\_1$. As a second AI module $K1\_2$, the preoperative artificial intelligence K1 comprises for example an artificial intelligence for preoperative pathology recognition. The preoperative data $D1\_2$ to $D1\_4$ are supplied to both AI modules $K1\_1$ and $K1\_2$. The results of the AI module $K1\_1$ are transferred via the transfer point P2 to the intraoperative artificial intelligence K2; likewise, the results of the second AI module $K1\_2$ are transferred via the transfer point P3 to the intraoperative artificial intelligence K2.

Data processed by the preoperative artificial intelligence K1 are output via the transfer points P2 and P3 as preoperative output data and received by the intraoperative artificial intelligence K2 as input data. In addition to these data, the intraoperative artificial intelligence K2 also processes the intraoperative data D2.

The intraoperative data D2 are for example image data $D2\_1$ and $D2\_2$ from cameras in the operation room, or image data $D2\_3$ from a camera that provides a live image of the operating table. Furthermore, the intraoperative data D2 can be image data $D2\_4$ from an endoscope camera. The medical system therefore comprises various cameras as intraoperative data sources.

In addition to image data, the intraoperative data D2 also comprise for example data from an electrosurgical generator, wherein a distinction is to be drawn between the settings and parameters $D2\_5$ of the electrosurgical generator and device information $D2\_6$. Likewise, the intraoperative data D2 can comprise data from an ultrasonic generator, wherein a distinction is also drawn between the settings and parameters $D2\_7$ and the device information $D2\_8$.

The intraoperative artificial intelligence K2 delivers live images that are provided with identifiers or notes as user output, for example to a first output module $8\_1$ that can be a screen. These are in particular live images with an expanded depiction of reality (augmented reality). For example, the parameters of an electrosurgical generator or the settings of an ultrasonic generator are displayed on the other output modules $8\_2$, $8\_3$ which can also be screens or displays.

The data are processed in the intraoperative artificial intelligence by various AI modules $K2\_1$ to $K2\_9$. The intraoperative artificial intelligence comprises an AI module as the first AI module $K2\_1$ which is configured to recognize a phase or a state of the performed surgical procedure. This AI module K2_1 receives preoperative data in the form of the operation plan D1_1. In addition, the AI module K2_1 receives image data D2_1 and D2_2 from the camera in the operating room as well as image data D2_3 from the camera of the operating table. This can be live data. The AI module K2_1 that recognizes the phase of the medical procedure forwards its results to the AI module K2_2 which is configured to provide image data with notes (also frequently termed "annotation engine"). This AI module K2_2 delivers for example the data for the screen 8_1 on which for example a live image provided with notes from the camera directed toward the operating table is reproduced. That is, after they are processed by the AI module 2_1, the data from the intraoperative data source D2_3 are provided in the AI module K2_2 with notes and then portrayed on the screen 8_1.

The AI module K2_1 also delivers its results, however, to the AI module K2_3 that provides user support (often frequently termed "assistance engine"). As an output, the AI module K2_3 delivers data that are portrayed on the screens or displays 8_2 and 8_3 and that relate to settings or the state of the electrosurgical generator, or the ultrasonic generator.

The AI module K2_1 also forwards its results to an AI module K2_4 in which recognition of specific identifiers occurs (often also termed "landmark recognition"). For this, this AI module K2_4 also receives intraoperative data in the form of image data D2_4 of a live image from the endoscope used. The AI module K2_1 also delivers its data to an AI module K2_5 in which object recognition occurs. The AI module K2_5 that performs the object recognition furthermore receives intraoperative data in the form of camera image data D2_1 to D2_3. The AI module K2_4 delivers its results to another AI module K2_6 that performs intraoperative anatomy and pathology recognition. The results from this AI module are again provided to the AI module K2_2 and the AI module K2_3. The AI module K2_5 also delivers its results to another AI module K2_7 that performs instrument recognition in for example the image data provided by the endoscope. For this, this AI module K2_7 also receives the live image from the endoscope in the form of the intraoperative data D2_4. The results are provided to the AI module K2_2.

All of the data that relate to the medical devices used, i.e., the electrosurgical generator and ultrasonic generator in the illustrative case, are supplied in the AI module K2_8 that performs a processing of the device data. The AI module K2_8 therefore receives the intraoperative data 2_5 to D2_8. The result is again provided by this AI module to the AI modules K2_2 and the AI module K2_3. Moreover, using the endoscope live image D2_4, a depth calculation is performed by the AI module K2_9, the results of which are provided to the AI module K2_6.

The individual AI modules K2_1 to K2_9 of the intraoperative artificial intelligence K2 can be combined with each other as desired and linked into groups. The same holds true for the individual AI modules K1_1 and K1_2 from the preoperative artificial intelligence K1.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

2 Medical system
4 Preoperative data source
6 Intraoperative data source
8 Output unit
8_1 to 8_3 Output modules
K1_1, K1_2 AI modules
K1 Preoperative artificial intelligence
K2_1 to K2_9 AI modules
K2 Intraoperative artificial intelligence
D1_1 to D1_4 Preoperative data
D1 Preoperative data
D2_1 to D2_8 Intraoperative data
D2 Intraoperative data
P1, P2, P3 Transfer points

The invention claimed is:

1. An operating method for performing a surgical procedure by one or more processors configured to implement a plurality of intraoperative artificial intelligence modules, the operating method comprising:
  receiving, by the one or more processors, intraoperative data comprising one or more parameters and operating data of at least one operated medical device operated during the surgical procedure;
  generating, by the one or more processors, notes based on the one or more parameters and operating data of the at least one operated medical device operated during the surgical procedure;
  receiving, by the one or more processors, as the intraoperative data, second image data of live images captured during the surgical procedure by one or more cameras;
  processing, by the one or more processors, the second image data to recognize at least one surgical instrument visible in the live images and used intraoperatively;
  receiving, by the one or more processors, characteristic instrument parameters and operating data generated by the at least one surgical instrument recognized;
  generating, by the one or more processors, the notes based on the characteristic instrument parameters and operating data received;
  generating, by the one or more processors, augmented reality data of augmented reality live images in which the notes based on the one or more parameters and operating data of the at least one operated medical device operated during the surgical procedure are superimposed on the live images;
  controlling one or more screens to display the augmented reality live images based on the augmented reality data generated;
  generating, by the one or more processors, device information that characterizes one or more of an operating state and a configuration of the at least one operated medical device;
  processing, by the one or more processors, the second image data to recognize a method status of the surgical procedure; and
  generating, by the one or more processors, the device information of the at least one operated medical device while additionally taking into account the status of the surgical procedure recognized.

2. The operating method according to claim 1, wherein the one or more processors are configured to implement a plurality of preoperative artificial intelligence modules, the operating method further comprising:
  supplying, to the one or more processors, as preoperative data, first image data of preoperatively acquired images acquired by at least one imaging medical device; and generating, from the first image data, anatomical data of one or more of an anatomy and a pathology present in the preoperatively acquired images.

3. The operating method according to claim 2, further comprising:
generating, by the one or more processors, the notes based on the anatomical data of the one or more of the anatomy and the pathology present in the preoperatively acquired images.

4. The operating method according to claim 3, further comprising:
performing, by the one or more processors, one or more of indicator recognition on the second image data to recognize an indicator in the live images and object recognition on the second image data to recognize an object in the live images; and
generating, by the one or more processors, the notes based on the anatomical data of the one or more of the anatomy and the pathology present in the preoperatively acquired images while additionally taking into account one or more of the indicator recognized by the indicator recognition and the object recognized by the object recognition.

5. The operating method according to claim 1, further comprising:
processing, by the one or more processors, the second image data to recognize a method status of a surgical procedure; and
generating, by the one or more processors, the notes based on the method status of the surgical processor recognized.

6. The operating method according to claim 2, further comprising:
generating, by the one or more processors, device information of the at least one operated medical device while additionally taking into account the anatomical data of the one or more of the anatomy and the pathology present in the preoperatively acquired images.

7. The operating method according to claim 1, wherein the individual processing steps are performed in individual modules of the plurality of intraoperative artificial intelligence modules.

8. The operating method according to claim 7, wherein the individual modules of the plurality of intraoperative artificial intelligence modules are combined into one module group, wherein the individual modules are linked together such that output data of a first module of the individual modules is supplied as input data to a second module of the individual modules.

9. A medical system for performing a surgical procedure, the medical system comprising:
one or more processors configured to implement a plurality of intraoperative artificial intelligence modules to:
receive, as intraoperative data, one or more parameters and operating data of at least one operated medical device operated during the surgical procedure;
generate notes based on the one or more parameters and operating data of the at least one operated medical device operated during the surgical procedure;
receive, as the intraoperative data, second image data of live images captured during the surgical procedure by one or more cameras;
process the second image data to recognize at least one surgical instrument visible in the live images and used intraoperatively;
receive characteristic instrument parameters and operating data generated by the at least one surgical instrument recognized;
generate the notes based on the characteristic instrument parameters and operating data received;
generate augmented reality data of augmented reality live images in which the notes based on the one or more parameters and operating data of the at least one operated medical device operated during the surgical procedure are superimposed on the live images;
control one or more screens to display the augmented reality live images based on the augmented reality data generated;
generate device information that characterizes one or more of an operating state and a configuration of the at least one operated medical device;
process the second image data to recognize a method status of the surgical procedure; and
generate the device information of the at least one operated medical device while additionally taking into account the status of the surgical procedure recognized.

* * * * *